United States Patent [19]

Kastron et al.

[11] 4,435,574
[45] Mar. 6, 1984

[54] 2,6-DIMETHYL-3,5-DICARBOMETHOXY-4-(ORTHO-DI-FLUOROMETHYLTHIO-PHENYL)-1,4-DIHYDROPYRIDINE

[76] Inventors: Valeria V. Kastron, ulitsa Avo tu, 33, kv. 2; Rasma O. Vitolin, ulitsa Suvorova, 117, kv. 13; Gunar Y. Dubur, ulitsa Ierikju, 43, kv. 2, all of Riga; Marita Y. Selga, ulitsa Kursas, 1, Rizhsky raion, selo Garkalne; Guntis V. Zarinsh, ulitsa Lachu, 5, kv. 1, Riga; Natalya V. Kondratenko, Rusanovskaya naberezhnaya, 6, kv. 171, Kiev; Vladimir I. Popov, ulitsa Bratislavskaya, 2, kv. 86, Kiev; Alexandr A. Kolomeitsev, prospekt 40 let Oktyabrya, 21, kv. 204, Kiev; Lev M. Yagupolsky, ulitsa Ivana Kudri, 41, kv. 48, Kiev, all of U.S.S.R.

[21] Appl. No.: 398,910

[22] Filed: Jul. 16, 1982

[30] Foreign Application Priority Data

Jul. 20, 1981 [SU] U.S.S.R. ............... 3353822

[51] Int. Cl.$^3$ .......................................... C07D 213/55
[52] U.S. Cl. ..................................... 546/321; 424/266
[58] Field of Search ................................. 546/321, 322

[56] References Cited

U.S. PATENT DOCUMENTS 3,968,117 7/1976 Bossert et al. ....................... 546/321

OTHER PUBLICATIONS

Kastron et al., Chemical Abstracts, vol. 91, No. 19, Abst. No. 157,609g, Nov. 5, 1979.

Primary Examiner—Alan L. Rotman
Attorney, Agent, or Firm—Lilling and Greenspan

[57] ABSTRACT

The present invention relates to derivatives of 1,4-dihydropyridine and, more specifically, to 2,6-dimethyl-3,5-dicarbomethoxy-4-(o-difluoromethylthiophenyl)-1,4-dihydropyridine having the formula

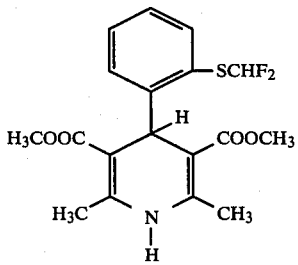

The proposed compound features pronounced hypotensive activity of prolonged duration and is capable of producing a coronarodilating effect while having low toxicity and being useful for treating diseases of the cardiovascular system.

1 Claim, No Drawings

2,6-DIMETHYL-3,5-DICARBOMETHOXY-4-(ORTHO-DI-FLUOROMETHYLTHIOPHENYL)-1,4-DIHYDROPYRIDINE

FIELD OF THE INVENTION

The present invention relates to derivatives of 1,4-dihydropyridine and, more specifically, to 2,6-dimethyl-3,5-dicarbomethoxy-4-(o-difluoromethylthiophenyl)-1,4-dihydropyridine.

2,6-dimethyl-3,5-dicarbomethoxy-4-(o-difluoromethylthiophenyl)-1,4-dihydropyridine features hypotensive activity of prolonged duration and is capable of producing a coronarodilating effect, which makes it useful for medicine.

BACKGROUND OF THE INVENTION

There are known in the prior art a great many 1,4-dihydropyridine derivatives that possess hypotensive or coronarodilating activity.

One specific prior-art 1,4-dihydropyridine derivative is 2,6-dimethyl-3,5-dicarbothoxy-4-(o-trifluoromethylphenyl)-1,4-dihydropyridine known as SKF-24260 (see U.S. Pat. No. 3,511,847):

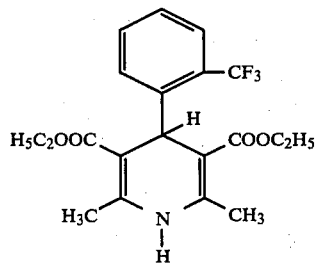

This compound features an appreciable hypotensive activity ($ED_{30}=0.022$ mg/kg).

However, the hypotensive effect produced by said compound is of short duration.

Besides, said compound is characterized by high toxicity ($LD_{50}=38.5$ mg/kg), which makes it practically impossible to be utilized medically on a wide scale.

Another prior-art 1,4-dihydropyridine derivative is 2,6-dimethyl-3,5-dicarbomethoxy-4-(o-nitrophenyl)-1,4-dihydropyridine (see U.S. Pat. No. 3,644,627):

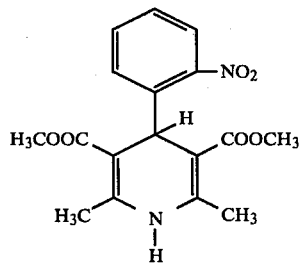

This compound is commercialized under the trade names of Adalate, Corinfar, and Nifedipine. It features high coronarodilating activity coupled with low toxicity, which assures it a wide field of application in medical practice.

However, this compound is highly sensitive to light, decomposing rapidly in the presence of light.

A further 1,4-dihydropyridine derivative known to the prior art is 2,6-dimethyl-3,5-dicarbomethoxy-4-(o-difluoromethoxyphenyl)-1,4-dihydropyridine (see U.K. Pat. No. 2,013,186):

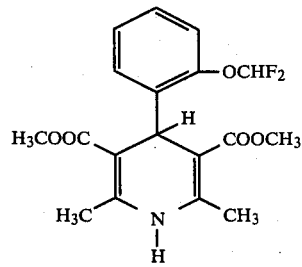

This compound is known under the trade name of Ryosidine.

Said compound features effective hypotensive activity ($ED_{30}=0.024$ mg/kg) and low toxicity.

However, the hypotensive action of said compound is of short duration.

SUMMARY OF THE INVENTION

The object of the present invention is to provide a 1,4-dihydropyrine derivative that features hypotensive activity of prolonged duration coupled with a coronarodilating effect.

This object is attained, in accordance with the invention, by the provision of a novel compound, namely 2,6-dimethyl-3,5-dicarbomethoxy-4-(o-difluoromethylthiophenyl)-1,4-dihydropyridine having the formula

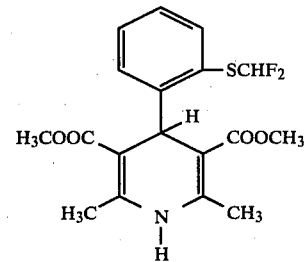

The aforesaid compound is pharmacologically active. It possesses hypotensive activity of prolonged duration coupled with a coronarodilating effect.

The effective dose of said compound, that will reduce the arterial blood pressure of anesthetized cats by 30 percent ($ED_{30}$), is 0.019 mg/kg, which practically coincides with the respective values established for SKF-24260 ($ED_{30}=0.022$ mg/kg) and for Ryosidine ($ED_{30}=0.024$ mg/kg). It has been established by experimentation with spontaneously hypertensive rats, that the hypotensive activity of the proposed compound is 3 times as high as that of the SKF-24260 compound. It is likewise essential that the duration of hypotensive action of the proposed compound be approximately 3 times as long as that established for SKF-24260.

Also, the toxicity of said compound ($LD_{50}=93$ mg/kg) is considerably lower than the SKF-24260 compound ($LD_{50}=38.5$ mg/kg).

It has also been established that the proposed compound produces a coronarodilating effect comparable with that of Adalate, a prior-art coronarodilating agent.

Considering the highly prolonged hypotensive activity of the proposed compound in the case of both oral and intravenous administration, and also the pronounced coronarodilatory action of said compound coupled with the low toxicity thereof, it can be concluded that the proposed compound is of great practical interest and can be used medicinally for treating diseases of the cardiovascular system.

DETAILED DESCRIPTION OF THE INVENTION

The proposed compound having the aforestated formula, can be prepared by condensation of methyl acetoacetate, o-difluoromethyl thiobenzaldehyde and ammonia while boiling in an inert organic solvent. The product is a light-resistant colorless crystalline substance which is soluble in organic solvents and insoluble in water.

Investigation of the pharmacological action of 2,6-dimethyl-3,5-dicarbomethoxy-4-(o-difluoromethylthiophenyl)-1,4-dihydropyridine upon parameters characterizing the performance of the cardiovascular system has been carried out in anesthetized cats, as well as in rats.

In experiments with spontaneously hypertensive female rats of the Okamoto-Aoki line, which were kept awake, with the proposed compound administered into the stomach in doses of 1 mg/kg and 10 mg/kg, the systolic arterial pressure dropped considerably (see Table 1).

In the conditions as stated above, the proposed compound exceeded the SKF-24260 compound approximately 3 times with respect to both hypotensive activity and active period (see Table 1).

24 hours after administration of the proposed compound in a dose of 10 mg/kg, the systolic arterial pressure was down by a further 21.4±2.7%. Within the same period of time, the rats administered SKF-24260 in the same dose had their systolic arterial pressure return to the initial value or increase above the initial level.

In acute experiments carried out in anesthetized cats, administering the proposed compound in a 50% aqueous solution of dimethylacetamide, the same hypotensive effect can be observed as in the case of SKF-24260 administered similarly.

In experiments carried out in anesthetized cats while recording the volume rate of the coronary blood flow, the proposed compound administered intravenously in a dose of 0.05 to 0.1 mg/kg will increase the blood outflow from the sinus venosus coronarius by 103 to 150 percent within 30 to 65 minutes, this being comparable with the coronarodilatory action of Adalate, a drug widely used for the same purpose (see Table 2).

In experiments carried out in breedless white mice, the proposed compound, administered intraperitoneally, has been investigated for acute toxicity. The proposed compound is found to be considerably less toxic that the SKF-24260 compound (see Table 1).

An example illustrating preparation of 2,6-dimethyl-3,5-dicarbomethoxy-4-(o-difluoromethylthiophenyl)-1,4-dihydropyridine is given hereinunder.

6.8 g (4.0 mmol) of o-difluoromethyl thiobenzaldehyde, 9.26 g (8.0 mmol) of methyl acetoacetate, 6.2 ml of a concentrated aqueous solution of ammonia, and 20 ml of methanol are boiled for 3 hours. 11 g (71%) of 2,6-dimethyl-3,5-dicarbomethoxy-4-(o-difluoromethylthiophenyl)-1,4-dihydropyridine precipitate upon cooling. The precipitate is made to crystallize from ethanol, giving 8.2 g (53.2%) of a colorless substance having a melt temperature of 173° to 175° C.

UV spectrum, $\lambda_{max}$, nm (log $\epsilon$); 206 (4.4), 243 (4.3), 371 (3.8).

IR spectrum, $cm^{-1}$: 1623, 1646, 1694, 3352.

PMR spectrum, $\delta$, ppm (in $CDCl_3$): 2.21 (6H, s, 2.6—$CH_3$); 3.53 (6H, s, $OCH_3$); 5.47 (1H, s, 4—H); 6.78 (1H, t, $OCHF_2$); 7.18 (4H, m, aromat.). TLC, Silufol-254, cyclohexane-ethyl acetate (1:1), $R_f$=0.51

Calculated, %: C, 56.4; H, 5.0; N, 3.6. Found, %: C, 56.2; H, 4.9; N, 3.3. $C_{18}H_{19}F_2NO_4S$.

TABLE 1

Hypotensive activity and acute toxicity of 2,6-dimethyl-3,5-dicarbomethoxy-4-(o-difluoromethylthiophenyl)-1,4-dihydropyridine

| Compound | $ED_{30}$, mg/kg, cats | Hypotensive effect, %, upon administration to spontaneously hypertensive rats | | | | $LD_{50}$, mg/kg intraperitoneal administration to white mice |
|---|---|---|---|---|---|---|
| | | after 6 hours | | after 24 hours | | |
| | | 1 mg/kg | 10 mg/kg | 1 mg/kg | 10 mg/kg | |
| Proposed compound | 0.019 | 19.5±3.4 | 54.8±1.2 | Initial pressure | 21.4±2.7 | 93 |
| SKF-24260 | 0.022 | 6.0±3.9 | 15.8±5.9 | Initial pressure | Initial pressure | 38.5 |

TABLE 2

Effect of 2,6-dimethyl-3,5-dicarbomethoxy-4-(o-difluoromethylthiophenyl)-1,4-dihydropyridine upon the coronary blood flow in experiments carried out in cats

| Compound | Dose (mg/kg), intraveneous administration | Increase in coronary blood flow, % | Effective period, min. |
|---|---|---|---|
| Proposed compound | 0.05 | 103 | 30 |
| | 0.1 | 150 | 65 |
| Adalate | 0.05 | 90 | 35 |

We claim:
1. 2,6-dimethyl-3,5-dicarbomethoxy-4-(o-difluoromethylthiophenyl)-1,4-dihydropyridine having the formula

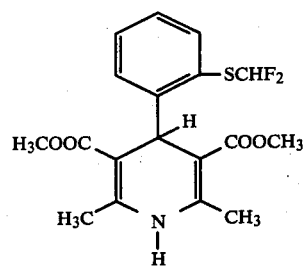

* * * * *